(12) United States Patent
Vinogradov-Nurenberg

(10) Patent No.: US 10,078,026 B2
(45) Date of Patent: Sep. 18, 2018

(54) MULTI-COMPONENT FORCE-TORQUE SENSING DEVICE WITH REDUCED CROSS-TALK FOR TWIST-COMPRESSION TESTING MACHINE

(71) Applicant: Michael Vinogradov-Nurenberg, Sunnyvale, CA (US)

(72) Inventor: Michael Vinogradov-Nurenberg, Sunnyvale, CA (US)

( * ) Notice: Subject to any disclaimer, the term of this patent is extended or adjusted under 35 U.S.C. 154(b) by 0 days.

(21) Appl. No.: 15/396,443

(22) Filed: Dec. 31, 2016

(65) Prior Publication Data
US 2017/0191888 A1 Jul. 6, 2017

Related U.S. Application Data

(60) Provisional application No. 62/273,609, filed on Dec. 31, 2015.

(51) Int. Cl.
| | |
|---|---|
| *G01L 5/22* | (2006.01) |
| *G01M 5/00* | (2006.01) |
| *G01N 3/00* | (2006.01) |
| *G01N 3/04* | (2006.01) |
| *G01L 5/16* | (2006.01) |
| *G01N 3/22* | (2006.01) |

(52) U.S. Cl.
CPC ............... *G01L 5/22* (2013.01); *G01L 5/161* (2013.01); *G01M 5/0075* (2013.01); *G01N 3/00* (2013.01); *G01N 3/04* (2013.01); *G01N 3/22* (2013.01); *G01N 2203/0482* (2013.01)

(58) Field of Classification Search
CPC ..... G01L 5/16; G01L 5/22; G01L 1/26; G01N 19/02
USPC ....................... 73/862.041–862.046
See application file for complete search history.

(56) References Cited

U.S. PATENT DOCUMENTS

| | | | |
|---|---|---|---|
| 4,412,198 A * | 10/1983 | Reich ...................... | H01F 38/18 336/120 |
| 5,795,990 A * | 8/1998 | Gitis ........................ | G01N 3/56 73/10 |
| 7,047,826 B2 | 5/2006 | Peshkin | |
| 8,671,780 B2 | 3/2014 | Kwom et al. | |
| 8,776,616 B2 | 7/2014 | Szasz et al. | |
| 9,448,128 B2 | 9/2016 | Kim et al. | |
| 9,618,416 B2 * | 4/2017 | Okada ................. | G01M 17/021 |

* cited by examiner

*Primary Examiner* — Jonathan Dunlap
*Assistant Examiner* — Octavia Hollington

(57) ABSTRACT

A multi-component force-torque sensing device contains force- and torque-sensitive elements mounted on a common base so that the axis of rotation of the measured torque coincides with the direction of action of the force being measured. The force and the torque are applied to a test specimen holder simultaneously. For reducing cross-talk between the sensitive elements installed on the base the test specimen holder is connected to the sensitive elements via a cross-talk reducing member with respective adapters which translate the force and the torque to the sensitive elements independently, without affecting or disturbing each other measurements.

9 Claims, 8 Drawing Sheets

MULTI-COMPONENT FORCE-TORQUE SENSING DEVICE WITH REDUCED CROSS-TALK FOR TWIST-COMPRESSION TESTING MACHINE

FIELD OF THE INVENTION

The present invention relates to the field of tribology and force and torque measurement technique, in particular to a method and apparatus for measuring forces and torques in a twist-compression friction testing machine and, more particularly, to multi-component sensing device for measuring a normal load and a friction torque in mechanical testers and tribometers. Also, the present invention relates to a sensing circuit for a force-torque sensing device and a method for measuring forces and torques. The invention further relates to a method for reducing cross-talk in a multi-component force-torque sensing device.

BACKGROUND OF THE INVENTION

Tribology is a science of friction, wear, and lubrication on friction surfaces. Mechanical testing machines and tribometers are used for testing parts, materials, coatings, lubricants, etc. for evaluating mechanical properties, durability, wear resistance, lubricity, etc. of tested specimens. In such mechanical testing machines tested specimens are subject to an axial (usually vertical) compression with simultaneous rotation around the axis of compression, thus performing so-called twist-compression, thrust washer, disc-on-disc, ring-on-disc, four-ball, drilling or tapping torque tests.

Various types of sensing devices based on strain-gauges and other techniques for monitoring and controlling the magnitude of applied forces and measuring torques are known in the art, such as the load cells and torque sensors manufactured and supplied by Measurement Specialties, Transducer Techniques, Omega Engineering, Interface Inc., and others. In order to measure simultaneously both the force and the torque applied to a workpiece a load cell and a torque sensor can be assembled together, one on top of another. An example of such an arrangement is shown schematically in FIG. 1, where a sensor assembly, which in general is designated by reference numeral 10 comprises a torque sensitive element or a torque sensor 11 attached to a force sensitive element or a load cell 12. This sensor assembly is used on a testing machine, which in FIG. 1 is represented by a sensor mounting plate 15. An upper test material specimen or probe 20 fixed in a holder 22 attached to the sensor assembly. In a course of a test the upper specimen 20 is centered and brought in contact with a lower disc-like test material specimen 24 fixed on a rotary drive coupled to a lower platform of the testing machine (not shown), which performs rotary motion in the direction indicated by arrow R, while being in contact with the stationary upper specimen 20. A loading force Fz applied to the upper specimen is monitored by the load cell 12, while a reaction torque Tz is measured by the torque sensor 11.

In another application, a force-torque sensor assembly 10 can be attached to the lower platform of the testing machine and the lower disc specimen 24 can be fixed in the holder 22, while the rotary drive with the upper specimen 20 can be attached to the mounting plate 15. In that case the upper specimen 20 is rotating while applying the loading force Fz on the stationary lower specimen 24.

Such a design not only results in increased the testing setup total length, but also can cause a significant mutual influence or cross-talk between the force and the torque sensitive elements and measurement channels, i.e., applied load Fz can affect the torque sensor 11 and vice versa, the torque Tz applied to the specimen 20 can affect the load cell 12, since the load cells are usually designed to withstand uniaxial tensile or compression forces and may not have enough immunity against a twisting torque. In turn, the torque sensors may react not only on a twisting torque but also have a significant sensitivity to applied axial load.

In order to reduce dimensions of measuring devices and of testing machines various multi-component sensing devices and/or transducers can be employed, such as the ones supplied, for example, by ATI Industrial Automation, Schunk, Interface, and some other manufacturers. Such sensing devices usually comprise a multi-beam elastic member with deformation-sensitive elements, which react on complex deformations caused by the forces and torques applied to the elastic member. The resulting output signal is being processed using a compliance matrix technique and the applied force and torque components resolved by using special computation algorithms.

For example, U.S. Pat. No. 9,448,128 issued in 2016 to B. Kim, at al. (schematically shown in FIG. 2), U.S. Pat. No. 8,776,616 issued in 2014 to P. Szasz, at al., U.S. Pat. No. 8,671,780 issued in 2014 to S. Kwom, at al., describe various multi-axial force-torque sensors, each of them typically comprising a central hub 120 (FIG. 2), an outer rim 121, a plurality of elastic members or beams 122 each having one side connected to the hub and the other side connected to the outer rim, and strain gauges 124 placed in defined areas on the beams to measure strain, from which forces and torques are calculated.

U.S. Pat. No. 7,047,826 issued in 2006 to M. Peshkin, describes a sensor (shown in FIG. 3) for measuring force and/or torque about a single axis or multiple axes, comprising a first inner member 220, a second outer member 230, an elastic member or a flexure 240 connecting the first member 220 and the second member 230, a handle 210 connected to the first inner member 220, mounting holes 250, and protective pins 260. Applying a force to the handle 210 moves the inner member 220 relative to the outer member 230 as controlled by the flexure 240. The amount or degree of the movement of the inner member 220 relative to the outer member 230 detected as a function of applied force and/or torque.

Performance and accuracy of such force-torque sensors may be affected significantly by structural errors due to the shape of elastic members and inaccuracy of the sensor body, as well as by signal processing errors, both resulting in a significant inter-channel cross-talk.

Another disadvantage of the multi-component force-torque sensors based on multi-beam elastic elements is the fact that such sensors have approximately similar sensitivity to all of the applied force and torque components, thus making it difficult to produce a sensor with significantly different working ranges for a loading force and a reaction torque.

Yet another disadvantage of the multi-component force-torque sensors based on multi-beam elastic elements is a complexity of their manufacturing processes and related to it their higher cost, and a fact that in case of a failure of a single beam the entire sensor becomes non-operational and non-repairable.

Thus, a need exists for a compact, reliable, and cost-effective multi-component force-torque sensor with increased mechanical stability and reduced cross-talk between the measured components.

OBJECTS OF THE INVENTION

It is an object of the present invention to provide a reliable and cost-effective multi-component sensor for measuring force and torque in twist-compression testing machines and tribometers, having increased mechanical stability and reduced cross-talk, which allows to increase its sensitivity, improve accuracy of measurements and increase dynamic range of forces and torques to be measured. Another object is to provide a method of measuring normal load and friction torque in tribometers and other mechanical testers and an apparatus for such a measurement.

SUMMARY OF THE INVENTION

According to one or several aspects of the invention, a multi-component force-torque sensing device with reduced cross-talk (hereinafter referred to merely as a "sensor device" or a "sensor") is provided. The invention also provides a method for reducing cross-talk in a multi-component force-torque sensing device. The sensor device of the invention also improves mechanical stability, sensitivity, improves accuracy of measurements and increases the dynamic range of forces and torques to be measured. The sensor device may find use in tribology and other fields that require simultaneous measurement of forces and torques.

According to one or several aspects of the invention, the proposed sensor device contains a mounting base, which supports a force transducer and a torque transducer positioned on the mounting base. The force transducer and the torque transducer are interconnected by a sensor cross-talk reducing member via respective adapters. The test specimen holder is movably connected with the force transducer via a force translating twisting adapter and with the torque transducer via a torque translating adapter in such a way that the applied force (e.g., a force transmitted as a reaction from the test specimens) is translated to the force transducer without affecting or disturbing the torque transducer, and the torque received by the test specimen holder (e.g., a friction torque transmitted from the interface between the test specimens) is translated to the torque transducer without affecting or disturbing the force transducer, thus reducing the cross-talk between the force and the torque measurements.

According to another aspect of the invention, the force translating twisting adapter is made rotatively movable in the direction of the applied torque, i.e., being able to rotate about an axis of rotation of the torque, and comprises at least one element capable of rotating while supporting a load, such as a thrust bearing, which supports the test specimen holder. This allows for an unrestricted rotation of the test specimen holder due to the action of the torque, which is translated by the sensor cross-talk reducing member to the torque transducer.

According to yet another aspect of the invention, the torque translating adapter is made moveable in the direction of the applied force so as not to interfere with the translation of the vertical force from the test specimen holder to the force transducer.

Another aspect of the invention provides an electric circuit for connecting the sensor device to a registration and measurement apparatus and for processing output signals from the force and the torque transducers.

Still another aspect of the present invention provides a method for measuring forces and torques, the method comprises providing a multi-component force-torque sensing device including a mounting base, a test specimen holder, a force transducer, a torque transducer, and a sensor cross-talk reducing member interconnecting the test specimen holder, the force transducer, and the torque transducer via respective adapters; the force-torque measurement method further including attaching the force-torque sensing device to a mechanical tester having a platform, a loading stage, a rotary drive, a first specimen, and a second specimen; coupling the first specimen to the force-torque sensing device and the second specimen to the rotary drive, causing a relative movement between the first specimen and the second specimen while applying a loading force to the loading stage thus developing the friction torque between the first and the second specimens, and causing output signals of the force transducer and of the torque transducer under effect of the loading force and the friction torque; and measuring the output signals in terms of the loading force and the friction torque, respectively.

The invention will be explained in more details below with reference to drawings in which illustrative embodiments of the invention are shown. It is understood that the drawings are intended for illustration purposes only without limitation of the scope of protection as defined by the subject matter of the appended claims.

DESCRIPTION OF THE INVENTION

Hereinafter, it is noted that only parts necessary to understand exemplary embodiments of the present invention will be described, and description of other parts will be omitted to avoid obscuring the subject matter of the present invention. As used herein, the terms "torque" and "moment of force" can be used interchangeably to refer to the turning action of a force or combined action of several forces applied to an object and causing rotation or twisting of the object relative to a reference pivot point or an axis about which the force may be considered as causing rotation.

Figure 1:
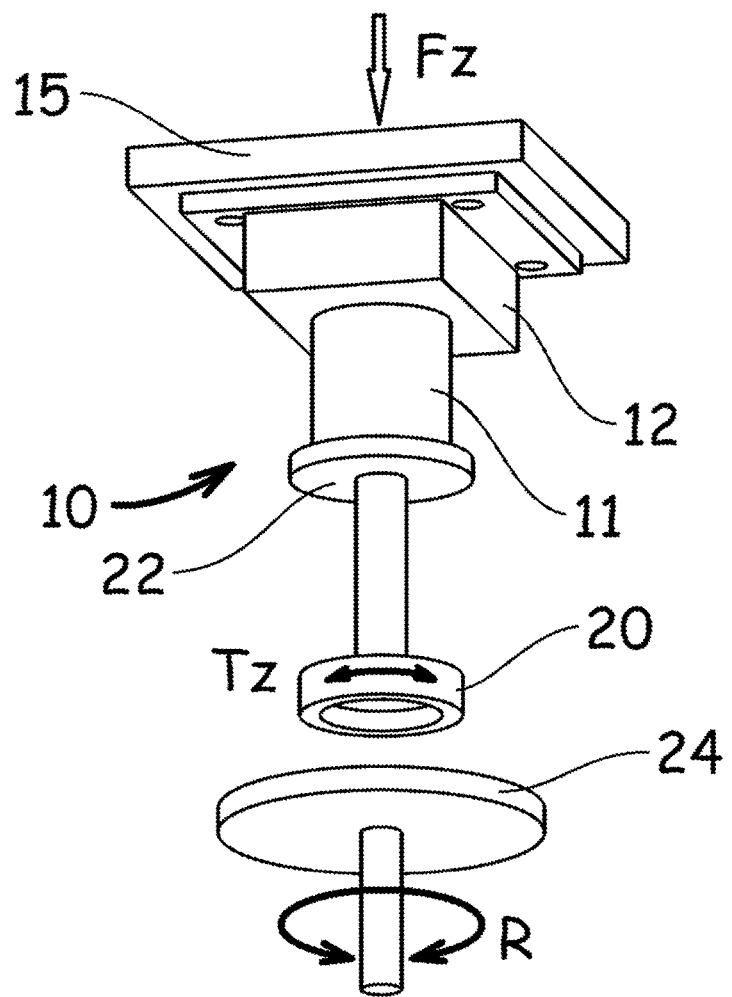
FIG. 1 is a perspective view of a known device for force and torque measurement in a twist-compression testing machine or in a mechanical tester.
Figure 2:
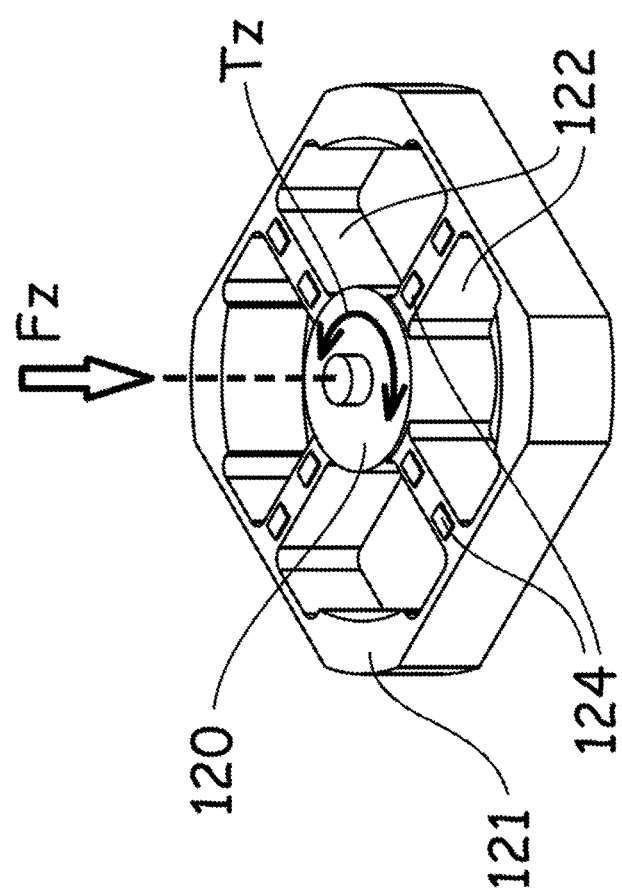
FIG. 2 is a perspective view of another known device for force and torque measurement based on a multi-beam elastic member.
Figure 3:
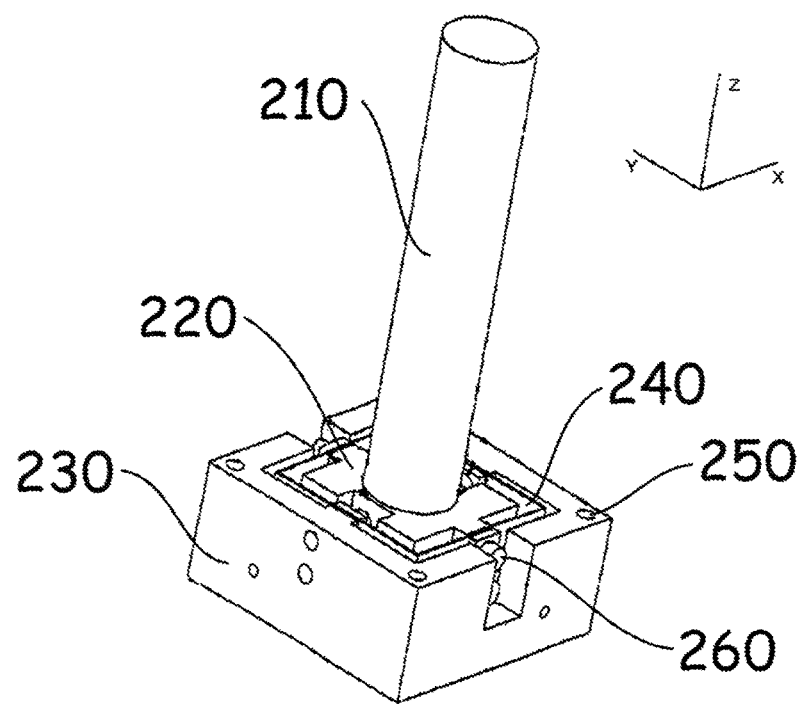
FIG. 3 is a perspective view of a yet another known device for force and torque measurement comprising multiple flexures and a handle.
Figure 4:
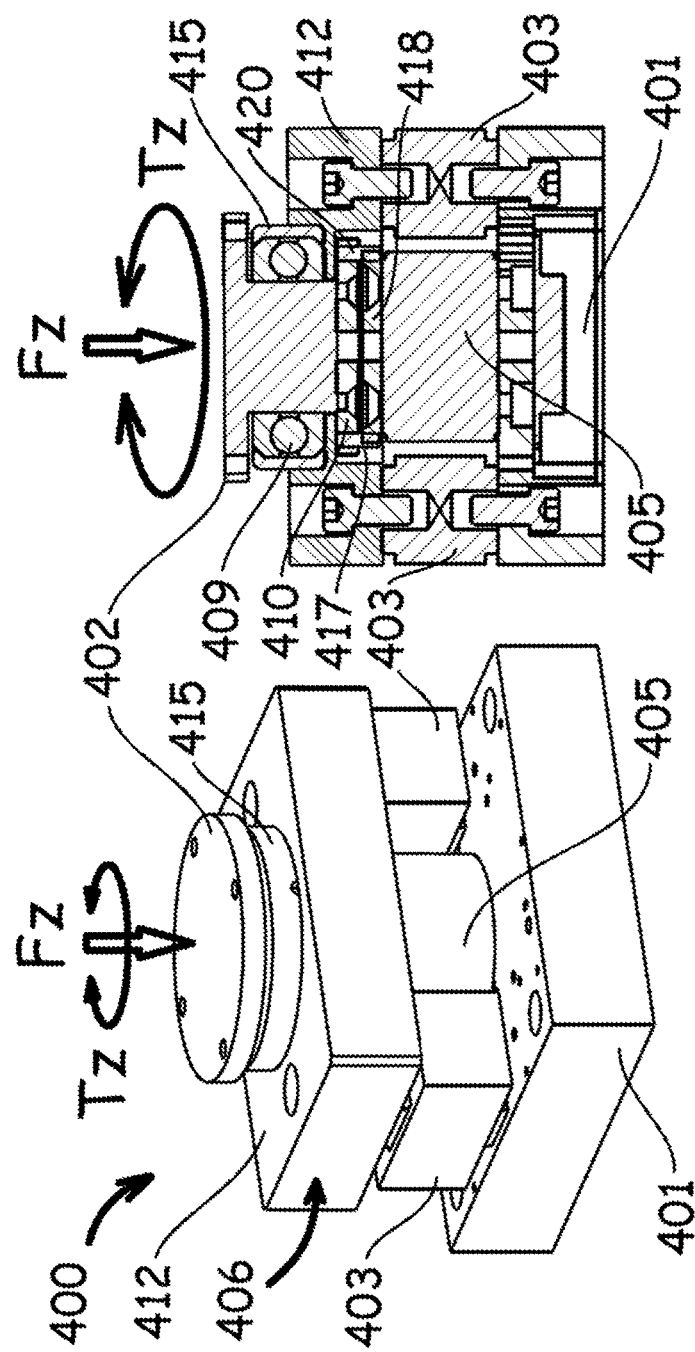
FIG. 4 is a perspective view and a cross-sectional view of a device of the invention for force and torque measurement in a twist-compression testing machine or in a mechanical tester.

Referring to the figures, wherein like parts are designated with like numerals and symbols, a sensor device of the invention, which in its entity is designated by reference numeral 400, is shown schematically in FIG. 4, which represents a perspective view and a cross-sectional view of the sensor. The sensor comprises a base 401 having a first mounting area and a second mounting area and having mounting holes for attaching the sensor device to a testing machine, a holder 402 for supporting a test specimen or a test probe and for receiving an applied force Fz and a torque Tz, a force transducer 403 attached to the base at the first mounting area for sensing the force Fz, a torque transducer 405 attached to the base at the second mounting area for sensing the torque, and a sensor cross-talk reducing member 406 interconnecting the force transducer, the torque transducer, and the holder and comprising a force translating twisting adapter 409 and a torque translating adapter 410. The force translating twisting adapter is movable in the direction of the torque Tz, i.e., being able to rotate about an axis of rotation of the torque in the direction indicated by arrows Tz in FIG. 4, while being capable of translating the force Fz from the holder to the force transducer without affecting or disturbing the torque transducer. The torque translating adapter is movable in the direction of the force Fz, while being capable of translating the torque Tz from the holder to the torque transducer without affecting or disturbing the force transducer, thus reducing the cross-talk between the force and the torque measurements in the sensor device.

In the embodiment presented in FIG. 4 the force translating twisting adapter 409 comprises a plate 412 attached to the force transducer 403 and a twisting element 415 mounted on the plate 412 and supporting the holder 402 in such a way that the holder can freely rotate under the action of the torque Tz, while translating the force Fz from the holder to the plate and to the force transducer without affecting or disturbing the torque transducer. In this embodiment, the torque translating adapter 410 comprises a movable element 417, which provides for an unrestricted motion in the direction parallel to the direction of the force Fz, while having a high torsional stiffness in the direction of the torque Tz. The torque Tz received by the specimen holder is translated through the movable element to the torque transducer without affecting or disturbing the force transducer, thus reducing the cross-talk between the force and the torque measurements.

In the embodiment presented in FIG. 4 the movable element 417 includes a disc with slots 418 attached to the torque transducer 405 and a plurality of pins 420 coupled to the test specimen holder 402 and slide-fitted into the slots in the disc 418 so that the pins can move in the slots in the direction parallel to the direction of the force Fz. The torque Tz received by the specimen holder is translated through the pins and through the slotted disc to the torque transducer without affecting or disturbing the force transducer, thus reducing the cross-talk between the force and the torque measurements. It is understood that the movable element 417 can be selected from a plurality of elements including shaft couplings, slotted-disc couplings, spider couplings, bellow couplings, magnet couplings, helical couplings, flexure couplings, chain couplings.

In the embodiment presented in FIG. 4 the twisting element 415 includes a thrust bearing mounted on the plate 412 and supporting the holder 402. It is understood that the twisting element 415 can be selected from a plurality of elements including thrust bearings, ball bearings, needle bearings, roller bearings, sliding bearings, angular contact bearings, air bearings, x-contact bearings, flexure suspensions.

Figure 5:
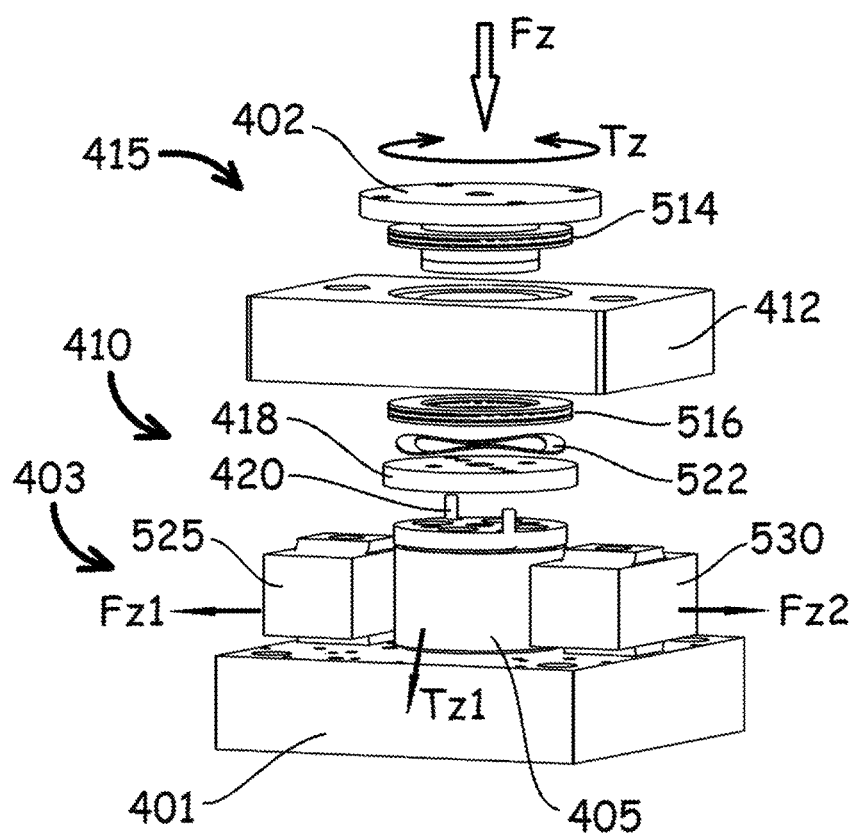
FIG. 5 is a perspective exploded view of another embodiment of the multi-component force-torque sensor of the invention.

It is further understood that the twisting element may include several bearings, as in another embodiment of the present invention shown in FIG. 5, which is a perspective exploded view of the multi-component force-torque sensor. In this embodiment, the twisting element 415 comprises two sets of thrust bearings 514 and 516 positioned at both sides of the plate 412 and preloaded by a spring 522. The torque translating adapter 410 comprises a slotted disc 418, which is attached to the specimen holder 402 having an extended shaft, and a plurality of pins 420 coupled to the torque transducer 405.

The load Fz applied to the specimen holder 402 translates through the thrust bearing 514 and the plate 412 to the force transducer 403 comprising two force-sensitive elements 525 and 530, thus causing corresponding changes of their output signals Fz1 and Fz2, respectively, proportional to a stress or a deformation induced in each force-sensitive element. The thrust bearing 516 and the spring 522 provide for a preload of the thrust bearing 514 while not restricting rotation of the specimen holder 402 due to the action of the measured torque Tz, thus improving vertical stability of the specimen holder assembly and repeatability and accuracy of the force and torque measurements. The torque translating adapter 410 having a low stiffness in the direction parallel to the applied load Fz doesn't restrict motion or deformation of the plate 412 and the force-sensitive elements 525 and 530 in this direction, thus not restricting translation of the applied force Fz from the specimen holder 402 through the thrust bearing 514 and the plate 412 to the force-sensitive elements 525 and 530, while preventing translation of the applied load Fz to the torque transducer 405, which allows for reducing the influence of the applied load Fz on the torque measurement.

The torque Tz applied to the specimen holder 402 causes the specimen holder with the attached slotted disc 418 to rotate. This rotation translates to the pins 420 coupled to the torque transducer 405, thus causing corresponding changes of an output signal of the torque transducer Tz1 proportional to a stress or a deformation induced in the torque transducer. The force translating twisting adapter with the twisting element 415 having low torsional stiffness doesn't restrict rotation of the specimen holder 402, while preventing translation of this rotation to the plate 412 and allowing for unrestricted translation of the torque Tz to the torque transducer 405, thus reducing the influence of the torque Tz on the force-sensitive elements 525 and 530.

Each of the force-sensitive elements 525, 530 attached to the base preferably in such a way that the directions of the maximum force sensitivity of the force-sensitive elements are parallel to each other and to the direction of the applied force Fz and perpendicular to the base 401. Notably, the distance between the force-sensitive elements 525 and 530 is greater than the dimension of the torque transducer 405. In the preferred embodiment, the torque transducer 405 attached to the base 401 between the force-sensitive elements 525 and 530 in such a way that the direction of the maximum torque sensitivity of the torque transducer is parallel to the direction of the applied torque Tz having the axis of rotation coinciding with the direction of the force Fz.

It is understood that the force-sensitive elements 525, 530 and the torque transducer 405 can be of any type and based on various modes of operation, including strain gauges, capacitive, inductive, piezo-electric, piezo-resonance, optical, and other sensors, used in connection with corresponding signal processing circuitry.

Figure 6:
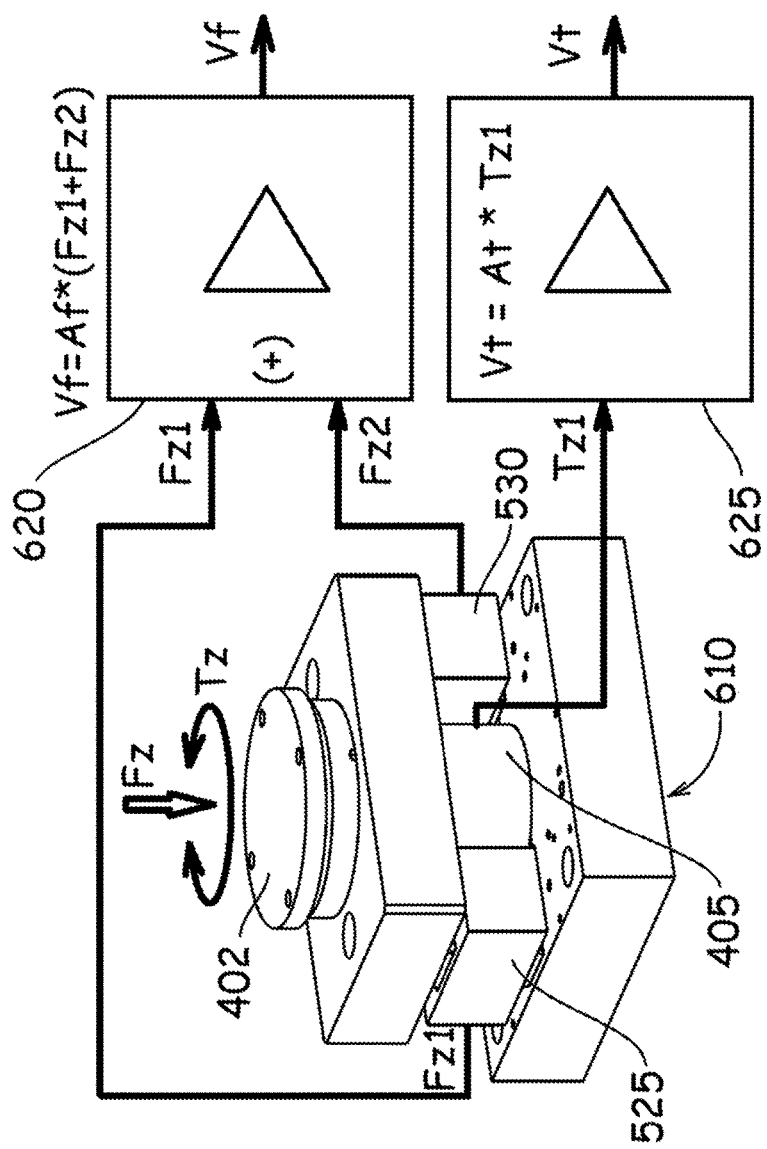
FIG. 6 is an example of an electric circuit for connecting a multi-component force-torque sensor device of the invention to the registration and measurement apparatus.

An example of a schematic diagram of a signal processing module 610 for the sensor device of invention is shown in FIG. 6, wherein the like parts are designated with the like numerals with the reference to FIG. 4 and FIG. 5. The output signals Fz1, Fz2 from the force sensitive elements 525, 530 of the force transducer are fed to a first signal processor 620 having a signal processing function Af, which generates the output voltage Vf proportional to the sum of the signals Fz1, Fz2 from the force-sensitive elements 525, 530, respectively, which in turn is proportional to the total magnitude of the load Fz applied to the holder 402. The output signal Tz1 from the torque transducer 405 is fed to a second signal processor 625 having a signal processing function At, which generates the output voltage Vt proportional to the magnitude of the torque Tz applied to the holder 402. The output voltages Vf and Vt can be measured and analyzed by any voltage measurement or data acquisition apparatus known in the art. The signal processing module 610 comprising the first signal processor 620 and the second signal processor 625 can be integrated within the sensor of invention, as shown in FIG. 6, or made as a separate module.

It is also understood that the output signals of the signal processors 620, 625 can be generated in a form of an output voltage, an output current, a charge, a signal frequency, or a digital code.

Figure 7:
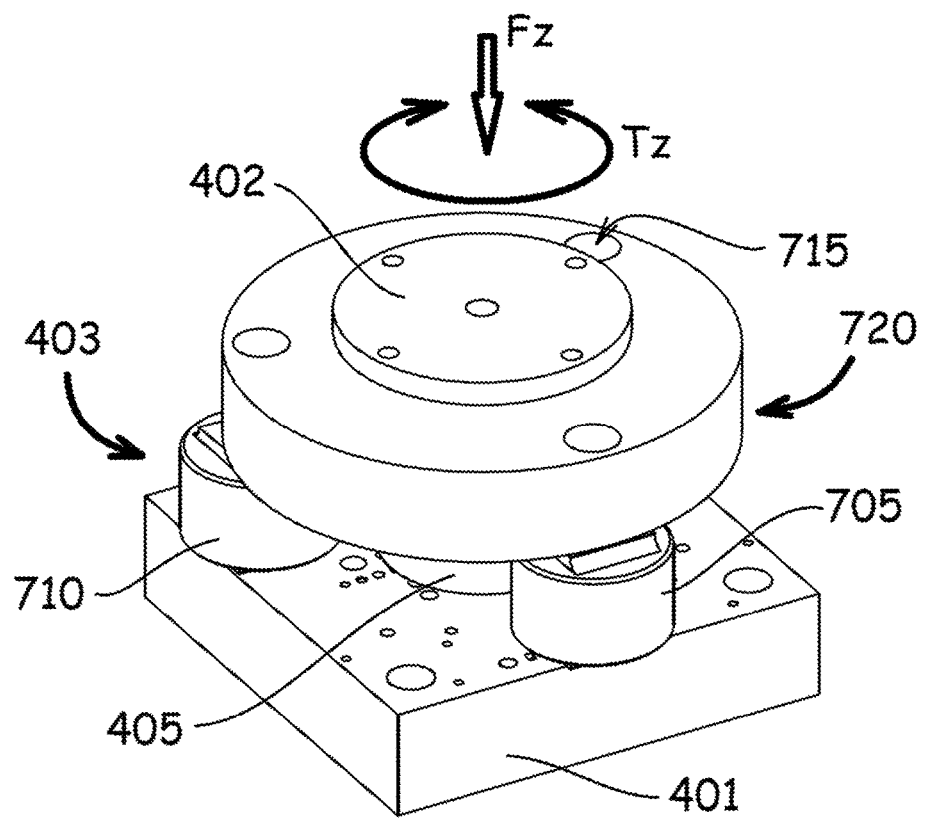
FIG. 7 is a perspective view of the multi-component force-torque sensor of the invention with three force-sensitive elements.

It is further understood that the force transducer can comprise more than two force-sensitive elements, as presented in the embodiment of the invention shown in FIG. 7, which is a perspective view of the multi-component force-torque sensor with the force transducer 403 comprising three force-sensitive elements 705, 710, and 715 attached to the base 401 in such a way that the directions of the maximum force sensitivity of all force-sensitive elements are parallel to each other and to the direction of the applied force Fz and perpendicular to the base 401. A sensor cross-talk reducing member 720 interconnects the force transducer 403, the torque transducer 405, and the holder 402 via the force translating twisting adapter and the torque translating adapter in such a way that the force Fz can be translated from the holder to the force-sensitive elements without affecting or disturbing the torque transducer, and the torque Tz can be translated from the holder to the torque transducer without affecting or disturbing the force transducer, thus reducing the cross-talk between the force and the torque measurements in the sensor device. In the preferred embodiment, the force-sensitive elements of the force transducer attached to the base symmetrically relative to the torque transducer. Similarly, the torque transducer 405 can comprise multiple torque-sensitive elements connected in such a way that the direction of the maximum torque sensitivity of each torque-sensitive element coincides with the direction of the applied torque.

Figure 8:
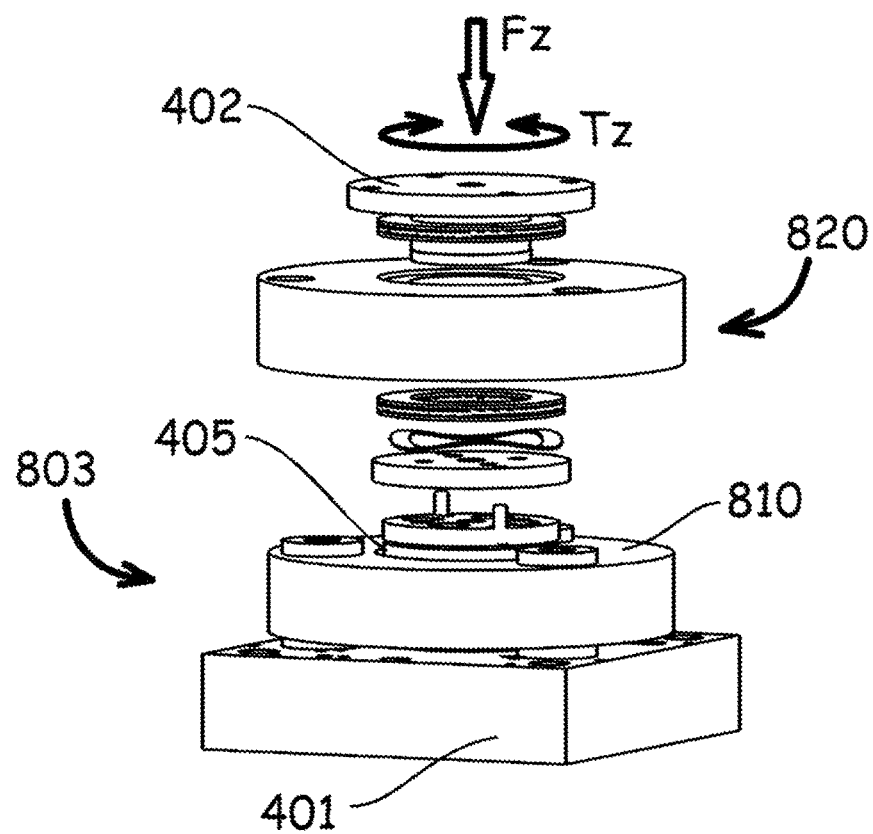
FIG. 8 is a perspective exploded view of yet another embodiment of the multi-component force-torque sensor of the invention with a toroidal-shaped force-sensitive element.

Another aspect of the invention illustrated in FIG. 8, wherein the force transducer 803 comprises a single force-sensitive element 810 having a toroidal or a doughnut-like shape, such as a ring load cell or a load washer, attached to the base 401 concentrically relative to the torque transducer 405. A sensor cross-talk reducing member 820 interconnects the force transducer 803, the torque transducer 405, and the holder 402 via the force translating twisting adapter and the torque translating adapter in such a way that the force Fz can be translated from the holder to the force transducer without affecting or disturbing the torque transducer, and the torque Tz can be translated from the holder to the torque transducer without affecting or disturbing the force transducer, thus reducing the cross-talk between the force and the torque measurements in the sensor device. It is understood that the torque transducer can also have a toroidal shape and be attached to the base concentrically relative to the force transducer comprising a single force-sensitive element.

Still another aspect of the present invention provides a method for measuring forces and torques, the method includes providing a multi-component force-torque sensing device including a mounting base, a test specimen holder, a force transducer, a torque transducer, and a sensor cross-talk reducing member interconnecting the test specimen holder, the force transducer, and the torque transducer via respective adapters in such a way that the force applied to the holder can be translated from the holder to the force transducer without affecting or disturbing the torque transducer, and the torque applied to the holder can be translated from the holder to the torque transducer without affecting or disturbing the force transducer; the method further including: attaching the force-torque sensing device to a mechanical tester having a platform, a loading stage, a rotary drive, a first test specimen, and a second test specimen; coupling the first test specimen to the force-torque sensing device and the second test specimen to the rotary drive; causing a relative movement between the first test specimen and the second test specimen while applying a loading force to the loading stage thus developing the friction torque between the first and the second specimens and causing output signals of the force transducer and of the torque transducer under effect of the loading force and the friction torque; and measuring the output signals in terms of the loading force and the friction torque, respectively.

The invention has been described and illustrated in various aspects with reference to specific structures and drawings. It is understood, however, that these structures and drawings are given only as examples and should not be construed as limiting the area of application of the invention. Therefore, any changes and modifications are allowed provided that they do not depart from the scope of the attached claims. For examples, more than two force-sensitive elements can be used. The mounting base may have a shape different from a flat. The adapters may have different shapes and designs, and the sensor device of the invention may be used not necessarily on a tribometer but on any other apparatus where simultaneous measurement of force and torque is needed. It is understood that features in accordance with various aspects can be used in various combinations. For examples, the force translating twisting adapters as thrust or angular contact bearings can be combined with the torque translating adapters as bellows, spider couplings, slotted-disc couplings, or as other devices suitable for accomplishing the objects of the invention within the scope of the claims.

The invention claimed is:

1. A multi-component sensing device for measuring a force acting in a first direction and a torque having an axis of rotation coinciding with the first direction, with reduced cross-talk between the measured force and the measured torque, said multi-component sensing device comprising:
   a mounting base having a first mounting area and a second mounting area;
   a force transducer for sensing the force, said force transducer connected to the mounting base at the first mounting area;
   a torque transducer for sensing the torque, said torque transducer connected to the mounting base at the second mounting area;

a test specimen/probe holder for supporting a test specimen or a test probe, said test specimen/probe holder having an axis that coincides with the first direction;

a sensor cross-talk reducing member comprising a force translating twisting adapter and a torque translating adapter, wherein the force translating twisting adapter is rigid in the first direction and is rotatively moveable about an axis coinciding with the first direction and connects the test specimen/probe holder with the force transducer, while the torque translating adapter is moveable in the first direction and having a high torsional stiffness in the direction perpendicular to the first direction and connects the test specimen/probe holder with the torque transducer.

2. The multi-component sensing device according to claim 1, wherein the torque transducer comprises at least one torque-sensitive element selected from the group consisting of a strain gauge sensor, a piezo sensor, a capacitive sensor, an inductive sensor, an optical sensor, and an opto-electronic sensor; said torque-sensitive element producing an output signal proportional to applied torque; said torque transducer further comprises a signal processing module having at least one input and one output; said at least one torque-sensitive element connected to said at least one input of the signal processing module; said signal processing module produces an output signal proportional to the input signal.

3. The multi-component sensing device according to claim 1, wherein said force transducer comprises at least two force-sensitive elements, each selected from the group consisting of a strain gauge sensor, a piezo sensor, a capacitive sensor, an inductive sensor, an optical sensor, and an opto-electronic sensor; said at least two force-sensitive elements each producing an output signal proportional to applied force; said force transducer further comprises a signal processing module having at least two inputs and one output; said at least two force-sensitive elements connected to said at least two inputs of the signal processing module; said signal processing module produces an output signal proportional to the sum of input signals.

4. The multi-component sensing device according to claim 1, wherein said force transducer comprises at least one toroidal-shaped force-sensitive element selected from the group consisting of a strain gauge sensor, a piezo sensor, a capacitive sensor, an inductive sensor, an optical sensor, and an opto-electronic sensor; said at least one toroidal-shaped force-sensitive element connected to said mounting base concentrically with respect to said torque transducer; said at least one toroidal-shaped force-sensitive element producing an output signal proportional to applied force; said force transducer further comprises a signal processing module having at least one input and one output; said at least one toroidal-shaped force-sensitive element connected to said at least one input of the signal processing module; said signal processing module produces an output signal proportional to the input signal.

5. The multi-component sensing device according to claim 1, wherein said force translating twisting adapter comprises at least one thrust-supporting element selected from the group consisting of a ball bearing, a needle bearing, a roller bearing, a sliding bearing, a thrust bearing, an angular contact bearing, an air bearing, an x-contact bearing, a flexure suspension.

6. The multi-component sensing device according to claim 1, wherein said torque translating adapter comprises at least one movable element selected from the group consisting of a shaft coupling, a slotted-disc coupling, a spider coupling, a bellow coupling, a magnet coupling, a chain coupling, a helical coupling, a flexure coupling, a multi-disc coupling.

7. The method according to claim 6, wherein the first adapter is selected from the group consisting of a slotted-disc coupling, a bellow coupling, a shaft coupling, a spider coupling, a magnet coupling, a chain coupling, a helical coupling, a flexure coupling, and a multi-disc coupling and the second adapter is selected from the group consisting of a thrust bearing, a ball bearing, a needle bearing, a roller bearing, a sliding bearing, an angular contact bearing, an air bearing, an x-contact bearing, and a flexure suspension.

8. The method according to claim 6, comprising:
installing said multi-component force-torque sensing device in a friction tester having a platform, a loading stage, a rotary drive, a first specimen, and a second specimen, the force being a loading force and the torque being a friction torque;
attaching the mounting base to the loading stage or to the platform of the friction tester;
attaching the rotary drive to the platform or to the loading stage of the friction tester;
coupling the first specimen to the test specimen holder of the multi-component force-torque sensing device;
coupling the second specimen to the rotary drive;
causing a relative movement between the first specimen and the second specimen while applying the loading force to the loading stage thus developing the friction torque between the first and the second specimens;
causing output signals of the force transducer and of the torque transducer under effect of the loading force and the friction torque; and
measuring the output signals in terms of the loading force and the friction torque, respectively.

9. A method for reducing cross-talk in a multi-component force-torque sensing device comprising:
providing a multi-component force-torque sensing device having a mounting base, a test specimen holder for supporting a test specimen, a force transducer for sensing a force acting in a first direction and a torque transducer for sensing a torque having an axis of rotation coinciding with the first direction;
connecting the force transducer and the torque transducer with the test specimen holder via a cross-talk reducing member comprising two adapters one of which is moveable in the first direction and another one is rotatively moveable about an axis coinciding with the first direction, whereby during measurement of the force and the torque it becomes possible to exclude influence of the force on the torque transducer and exclude influence of the torque on the force transducer.

* * * * *